United States Patent
Lemire et al.

(12)

(10) Patent No.: US 10,285,954 B2
(45) Date of Patent: *May 14, 2019

(54) TOPICAL USE OF AN ANTIMICROBIAL FORMULATION

(71) Applicant: Laboratoire M2, Sherbrooke (CA)

(72) Inventors: Gaetan Lemire, Sherbrooke (CA); Ulysse Desranleau Dandurand, Sherbrooke (CA); Sylvain Quessy, Ste-Anne-de-Sorel (CA); Ann Letellier, Massueville (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/654,025

(22) Filed: Jul. 19, 2017

(65) Prior Publication Data

US 2017/0312231 A1 Nov. 2, 2017

Related U.S. Application Data

(63) Continuation-in-part of application No. 13/790,911, filed on Mar. 8, 2013, now Pat. No. 9,750,245.

(51) Int. Cl.
| | |
|---|---|
| *A61K 31/05* | (2006.01) |
| *A61K 47/10* | (2017.01) |
| *A61K 47/18* | (2017.01) |
| *A61K 47/20* | (2006.01) |
| *A61K 47/12* | (2006.01) |
| *A61K 9/00* | (2006.01) |
| *A01N 31/08* | (2006.01) |
| *A01N 31/16* | (2006.01) |
| *A61K 47/44* | (2017.01) |
| *A61K 47/46* | (2006.01) |

(52) U.S. Cl.
CPC ............ *A61K 31/05* (2013.01); *A01N 31/08* (2013.01); *A01N 31/16* (2013.01); *A61K 9/0014* (2013.01); *A61K 9/0017* (2013.01); *A61K 47/10* (2013.01); *A61K 47/12* (2013.01); *A61K 47/183* (2013.01); *A61K 47/20* (2013.01); *A61K 47/44* (2013.01); *A61K 47/46* (2013.01)

(58) Field of Classification Search
CPC .. A61K 31/05; A61K 9/0017; A61K 91/0014; A61K 91/0017; A01N 31/08; A01N 25/04; A01N 25/02; A01N 65/00
See application file for complete search history.

(56) References Cited

U.S. PATENT DOCUMENTS

| | | | |
|---|---|---|---|
| 6,884,763 | B2 | 4/2005 | Willard et al. |
| 8,293,286 | B2 | 10/2012 | Nouvel |
| 2003/0225003 | A1 | 12/2003 | Ninkov |
| 2009/0258098 | A1 | 10/2009 | Rolling et al. |
| 2009/0269394 | A1 | 10/2009 | Baker, Jr. et al. |
| 2010/0034907 | A1 | 2/2010 | Daigle et al. |
| 2010/0137451 | A1 | 6/2010 | DeMarco et al. |
| 2010/0272818 | A1 | 10/2010 | Franklin et al. |
| 2011/0206790 | A1 | 8/2011 | Weiss |
| 2011/0223114 | A1 | 9/2011 | Chakrabortty et al. |
| 2013/0034618 | A1 | 2/2013 | Swenholt |

FOREIGN PATENT DOCUMENTS

| | | |
|---|---|---|
| AU | 2009235913 A1 | 10/2009 |
| CA | 2567333 A1 | 1/2005 |
| CN | 1350435 A | 5/2002 |
| CN | 102083307 A | 6/2011 |
| CN | 102186341 A | 9/2011 |
| EP | 1178736 B1 | 2/2004 |
| JP | 2011516504 A | 5/2011 |
| WO | 0069277 A1 | 11/2000 |
| WO | 2009132343 A1 | 10/2009 |
| WO | 2010010320 A1 | 1/2010 |

OTHER PUBLICATIONS

Ali Khan, H.; "Efficiency of Alkaline Compound Preparations on the Treatment of Foot and Mouth Disease Lesions in Buffalo", Pakistan J. Agric. Res., vol. 6, No. 3, pp. 230-233, 1985.
Hartshorn et al.; "Short communication: Minimum bactericidal concentration of disinfectants evaluated for bovine digital Dermatitis-associated-Treponema phagedenis-like spirochetes", American Dairy Science Association, 2013.
Sokovic et al.; "Antifungal Activity of the Essential oil of *Thymus vulgaris* L. and Thymol on Experimentally Induced Dermatomycoses", Drug Development and Industrial Pharmacy, 2008.
Suplementary European Search Report of European Application 14760718.8 dated Aug. 1, 2016; Molina de Alba, Jose; Munich.
Inouye et al, "Combined Effect of Heat, Essential Oils and Salt on the Fungicidal Activity against Trichopython mentagrophytes in Foot Bath," Jpn. J. Med. Mycol, vol. 48, pp. 27-36, 2007.
International Search Report of PCT/CA2014/000174 dated Jun. 11, 2014; Cristina Belyea.
Benefect Natural Hand Sanitizer, Laboratoire M2, 2013.
Cleanwell All-Natural Hand Sanitizer Care Product, Laboratoire M2, 2013.
Definition of "Subject," Oxford Dictionary—American English, Accessed Dec. 6, 2013, pp. 1-2.

*Primary Examiner* — Lakshmi S Channavajjala
(74) *Attorney, Agent, or Firm* — Benoit & Cote, Inc.; Mathieu Miron

(57) ABSTRACT

The present document describes a method of preventing or treating a hoof bacterial infection on at least one hoof of a live hoofed animal having a bacterial presence thereon with an antibacterial formulation comprising: a) at least one antimicrobial isolated or synthetic phenolic compound of natural origin; b) at least one surfactant sufficient to form a solution or dispersion of said phenolic compound in water; c) a solvent for dissolving said phenolic compound; and d) a sufficient water quantity to make 100% (w/w).

34 Claims, No Drawings

TOPICAL USE OF AN ANTIMICROBIAL FORMULATION

CROSS-REFERENCE TO RELATED APPLICATIONS

This application is filed under 37 CFR 1.53(b) as a continuation-in-part application. This application claims priority under 35 USC § 120 of U.S. patent application Ser. No. 13/790,911 filed Mar. 8, 2013, the entire contents of which is incorporated by reference in its entirety.

BACKGROUND (a) Field

The subject matter disclosed generally relates to a method of reducing a microbial presence on a part of a subject by topically contacting the subject's part with an antimicrobial formulation for a time sufficient to reduce the microbial presence.

(b) Related Prior Art

Pathogens such as fungi, viruses, bacteria and bacterial spores are responsible for a plethora of human and animal health problems, as well as contamination of food and biological and environmental samples. The first step in microbial infections is generally attachment or colonization of skin or mucus membranes, followed by subsequent invasion and dissemination of the infectious microbe. The portals of entry of pathogenic bacteria are predominantly the skin and mucus membranes.

In spite of modern improvements in hygiene and infection prevention, human and livestock health has become an increasingly important public health issue. This has been due in part to the fact that infections caused by bacteria, viruses and fungi have increased as a result of travel and global interconnections.

Effective disease prevention is key in maintaining healthy human and animal populations. Over the years the improvement in and availability of vaccines has greatly assisted in the prevention of a large number of diseases. However, even well vaccinated human and animal population can succumb under severe challenge. Moreover, since vaccines are not available for all the diseases to be prevented, well planned and monitored bio-security program, coupled with an effective disinfection and vaccination program, are essential for maintaining the health of these populations.

Antimicrobials formulations play a vital role in any biosecurity system, both in the process of terminal disinfection and in the ongoing hygiene maintenance. Apart from relatively minor changes and improvements in formulations, there has been little innovation in human or livestock antimicrobial formulations and large-surface antimicrobial formulations development for some fifteen to twenty years.

A great many of the current antimicrobial formulations, including sanitizers and disinfectants, contain antimicrobial agents which are not naturally occurring. Typical antimicrobial agents used in sanitizers and disinfectants include chemical disinfectants such as phenolic compounds, quaternary ammonium compounds, strong oxidizer, formaldehyde and halogen containing compounds. Such materials are not of natural origin (i.e. not found in nature) and are prepared through chemical processing and synthesis. A great many of these "synthetic" disinfectants cause undesirable effects on both the environment and on human health.

Benefect Natural Hand Sanitizer is a thyme oil based hand cleaner. Hence Benefect's product can be applied on human skin for disinfecting hands. Although this is a thyme oil based antimicrobial for topical application on human skin, it does not include an antimicrobial isolated or synthetic phenolic compound of natural origin in combination with a surfactant, a solvent for dissolving the phenolic compound and an aqueous carrier.

CleanWell's hand sanitizer has 0.05% thyme oil as one of the ingredients as well as citric acid as per the detailed product material safety data sheet. Although this is a thyme oil based antimicrobial for topical application on human skin, it does not include an antimicrobial isolated or synthetic phenolic compound of natural origin in combination with a surfactant, a solvent for dissolving the phenolic compound and an aqueous carrier.

International Publication No. WO 2010/010320 discloses the use of a composition which comprises a 100% of carvacrol, thymol and p-cymene only as a therapeutic agent or disinfectant with broad spectrum antimicrobial activity. However, this document does not teach the topical use of an antimicrobial isolated or synthetic phenolic compound of natural origin in combination with a surfactant, a solvent for dissolving the phenolic compound and an aqueous carrier.

U.S. Pat. No. 8,293,286 discloses a method for killing parasites that includes the step of topically applying onto a companion animal a composition which includes a natural, non-synthetic active ingredient. However, the disclosed composition includes ingredients such as methyl salicylate and vanillin. However, this document does not teach the topical use of an antimicrobial isolated or synthetic phenolic compound of natural origin in combination with a surfactant, a solvent for dissolving the phenolic compound and an aqueous carrier.

U.S. Pat. No. 6,884,763 discloses a waterless hand cleaner formulation which includes an organic solvent, a quantity of water and a surfactant present to form a gelatinous emulsion. The gelatinous emulsion is loaded with 0.1 to 25 total weight percent of a natural essential oil having topical antimicrobial activity. However, this document does not teach the topical use of an antimicrobial isolated or synthetic phenolic compound of natural origin in combination with a surfactant, a solvent for dissolving the phenolic compound and an aqueous carrier.

US Patent Publication No. 2011/0223114 discloses an antimicrobial composition. It particularly relates to an antimicrobial composition for cleansing or personal care. However, this document does not teach the topical use of an antimicrobial isolated or synthetic phenolic compound of natural origin in combination with a surfactant, a solvent for dissolving the phenolic compound and an aqueous carrier.

US Patent Publication No. 2010/0272818 discloses compositions which include terpenes which are particularly suitable for treating plant infections, to methods of making such composition, and to methods of using them. However, the composition disclosed is in the form of liquid, pellets or tablets and may include hollow glucan particles or cell wall particles.

US Patent Publication No. 2011/0206790 discloses natural essential oil based foamable compositions to be used as antimicrobial substances which include essential oils as antimicrobial agent. Additionally, the composition includes a source of divalent copper ions.

US Patent Publication No. 2009/0258098 discloses an antifungal composition and penetrating carrier system for topical treatment of dermatophytic infection and secondary bacterial infections. The composition includes an excipient, a penetration enhancer and at least one antifungal essential oil component.

Moreover, US Patent Publication No. 2009/0269394 discloses a method for treating and completely curing fungal, yeast and/or mold infections in human subjects comprising the step of topically administering to a human subject in need an antifungal nanoemulsion composition. The composition includes an aqueous phase and about 1% to 80% of essential oil.

There is therefore a need for an improved method for reducing a microbial topical presence on a live subject without the health hazards and drawbacks of the prior art.

SUMMARY

According to an embodiment, there is provided a method of preventing or treating a hoof bacterial infection on at least one hoof of a live hoofed animal having a bacterial presence thereon, the method consisting of topically applying to the hoof an antibacterial formulation for a time sufficient to reduce the bacterial presence, the antibacterial formulation consisting of:
  a) one antibacterial isolated or synthetic phenolic compound of natural origin selected from the group consisting of thymol and carvacrol;
  b) at least one surfactant sufficient to form a solution or dispersion of the phenolic compound in water;
  c) a solvent for dissolving the phenolic compound;
  d) a pH adjusting agent; and
  e) a sufficient water quantity to make 100% (w/w).

The formulation may comprise from about 0.05% to about 25% (w/w) of the phenolic compound.

The formulation may comprise from about 0.1% to about 15% (w/w) of the surfactant.

The formulation may comprise from about 0.1% to about 40% (w/w) of the solvent.

The formulation may comprise from about 0.01% to about 5% (w/w) of the pH adjusting agent.

The phenolic compound may be thymol.

The surfactant may be selected from the group consisting of sodium lauryl sulfate, sorbitan stearate, sodium laureth sulfate, sarkosyl, cocamidopropyl betaine (CAPB), sodium lauryl ether sulfonate, alkyl benzene sulfonates, nonylphenol ethoxylate, sorbitan esters and ether ethoxylate.

The antibacterial formulation has a pH from about 1 to about 10.

The pH adjusting agent may be chosen from citric acid, lactic acid, hydrochloric acid, boric acid, acetic acid, sodium hydroxide, potassium hydroxide, sulfuric acid, calcium carbonate, ammonium carbonate, ammonium bicarbonate, ammonium citrate, sodium citrate, magnesium carbonate, sodium carbonate, monosodium phosphate, disodium phosphate, trisodium phosphate, monopotassium phosphate, dipotassium phosphate, tripotassium phosphate, Tris(hydroxymethyl) aminomethane (TRIS), paracetic acid, propionic acid, fumaric acid, sorbic acid, benzoic acid, phenylacetic acid, malic acid, tartaric acid, dehydroacetic acid, glycine, 2-amino-2methyl-1,3-propanediol (AMPD), N-(1, 1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid (TES), 2-(N-morpholino)ethanesulfonic acid (MES), N-[Tris(hydroxymethyl)methyl] glycine (Tricine); N-Tris(hydroxymethyl)methyl-3-aminopropanesulfonic acid (TAPS) and 3-N-Morpholino propanesulfonic acid (MOPS), piperazie-N,N'-bis[2-hydroxypropanesulphonic]acid (POPSO), or a combination thereof.

The hoof bacterial infection may be chosen from a hoof rot, hoof scald, hoof abscesses, and combinations thereof.

The topically applying may be with one of a spray, a bath, a footbath, a direct application, a wipe, a cream, an ointment, a gel, or an unguent.

The hoof bacterial infection may be a lesion.

The lesion may be one of an ulcer, a diabetic ulcer, a furuncle, a carbuncle, a fissure, a crack, or a blister.

The hoof bacterial infection may be one of a salmonella infection, an *E. coli* infection, a staphylococcal infection, a spirochete infection, an impetigo, an ecthyma, a carbunculosis, a folliculitis, an erysipelas, an african tick bite fever, an arcanobacterium haemolyticum infection, a botryomycosis, a brucellosis, a canker, a chlamydial infection, a chronic lymphangitis, a chronic recurrent erysipelas, a cutaneous anthrax infection, a cutaneous diphtheria infection, a cutaneous group B streptococcal infection, a cutaneous pasteurella hemolytica infection, a cutaneous streptococcus iniae infection, a dermatitis gangrenosa, a desert sore, a digital dermatitis, a ecthyma gangrenosuma erythrasma, a foot abscess, a furunculosis, a gas gangrene, a glanders, a gram-negative folliculitis, a helicobacter cellulitis, an infected oil gland, an interdigital dermatitis, an interdigital phlegmon, an Italian foot rot a leptospirosis, a Listeria monocytogenes infection, a listeriosis, a melioidosis, a necrotizing fasciitis, a pasteurellosis, a pododermatitis, a primary gonococcal dermatitis, a salmonellosis, a super foot rot, or a toxic shock syndrome.

The live hoofed animal may be livestock.

The live hoofed animal may be cattle.

The live hoofed animal may be a dairy cow.

According to another embodiment, there is provided a method of preventing or treating a hoof bacterial infection on at least one hoof of a live hoofed animal having a bacterial presence thereon, the method consisting of topically applying to the hoof an antibacterial formulation for a time sufficient to reduce the bacterial presence, the antibacterial formulation consisting of:
  a) one antibacterial isolated or synthetic phenolic compound of natural origin selected from the group consisting of thymol and carvacrol;
  b) at least one surfactant sufficient to form a solution or dispersion of the phenolic compound in water;
  c) a solvent for dissolving the phenolic compound; and
  d) a sequestering agent;
  e) a pH adjusting agent; and
  f) a sufficient water quantity to make 100% (w/w).

The phenolic compound may be from about 0.05% to about 25% (w/w) of the formulation.

The surfactant may be from about 0.1% to about 15% (w/w) of the formulation.

The solvent may be from about 0.1% to about 40% (w/w) of the formulation.

The formulation may comprise from about 0.01% to about 5% (w/w) of the pH adjusting agent.

The formulation may comprise from about 0.01% to about 10% (w/w) of the sequestering agent.

The phenolic compound may be thymol.

The surfactant may be selected from the group consisting of sodium lauryl sulfate, sorbitan stearate, sodium laureth sulfate, sarkosyl, cocamidopropyl betaine (CAPB), sodium lauryl ether sulfonate, alkyl benzene sulfonates, nonylphenol ethoxylate, sorbitan esters and ether ethoxylate.

The sequestering agent may be selected from the group consisting of ethylene diamine tetraacetic acid (EDTA) sodium salt, sodium gluconate, sodium citrate, citric acid, trisodium NTA, trisodium ethylene disuccinate, sodium phosphate and sodium choleate.

The pH of the antibacterial formulation has a pH from about 1 to about 10.

The pH adjusting agent may be chosen from citric acid, lactic acid, hydrochloric acid, boric acid, acetic acid, sodium hydroxide, potassium hydroxide, sulfuric acid, calcium carbonate, ammonium carbonate, ammonium bicarbonate, ammonium citrate, sodium citrate, magnesium carbonate, sodium carbonate, monosodium phosphate, disodium phosphate, trisodium phosphate, monopotassium phosphate, dipotassium phosphate, tripotassium phosphate, Tris(hydroxymethyl) aminomethane (TRIS), paracetic acid, propionic acid, fumaric acid, sorbic acid, benzoic acid, phenylacetic acid, malic acid, tartaric acid, dehydroacetic acid, glycine, 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid (TES), 2-(N-morpholino)ethanesulfonic acid (MES), N-[Tris(hydroxymethyl)methyl] glycine (Tricine); N-Tris(hydroxymethyl)methyl-3-aminopropanesulfonic acid (TAPS) and 3-N-Morpholino propanesulfonic acid (MOPS), piperazie-N,N'-bis[2-hydroxypropanesulphonic]acid (POPSO), or a combination thereof.

The hoof bacterial infection may be chosen from a hoof rot, hoof scald, hoof abscesses, and combinations thereof.

The topically applying may be with one of a spray, a bath, a footbath, a direct application, a wipe, a cream, an ointment, a gel, or an unguent.

The hoof bacterial infection may be a lesion.

The lesion may be one of an ulcer, a diabetic ulcer, a furuncle, a carbuncle, a fissure, a crack, or a blister.

The bacterial infection may be one of a salmonella infection, an *E. coli* infection, a staphylococcal infection, a spirochete infection, an impetigo, an ecthyma, a carbunculosis, a folliculitis, an erysipelas, an african tick bite fever, an arcanobacterium haemolyticum infection, a botryomycosis, a brucellosis, a canker, a chlamydial infection, a chronic lymphangitis, a chronic recurrent erysipelas, a cutaneous anthrax infection, a cutaneous diphtheria infection, a cutaneous group B streptococcal infection, a cutaneous pasteurella hemolytica infection, a cutaneous streptococcus iniae infection, a dermatitis gangrenosa, a desert sore, a digital dermatitis, a ecthyma gangrenosuma erythrasma, a foot abscess, a furunculosis, a gas gangrene, a glanders, a gram-negative folliculitis, a helicobacter cellulitis, an infected oil gland, an interdigital dermatitis, an interdigital phlegmon, an Italian foot rot a leptospirosis, a Listeria monocytogenes infection, a listeriosis, a melioidosis, a necrotizing fasciitis, a pasteurellosis, a pododermatitis, a primary gonococcal dermatitis, a salmonellosis, a super foot rot, or a toxic shock syndrome.

The live hoofed animal may be livestock.
The live hoofed animal may be cattle.
The live hoofed animal may be a dairy cow.
The following terms are defined below.

The term "about" is intended to mean a value includes an inherent variation of error for the device or the method being employed to determine the value.

The term "hard water" is intended to mean a water having a high concentration of dissolved minerals and solids.

The terms "phenolic compound", "natural origin", "phenolic compound of natural origin" is intended to mean a phenolic compounds that exist or are produced in nature. Such phenolic compounds can be extracted or isolated from their natural environment by any suitable means. Of course, such phenolic compounds can also be synthetically produced by the hand of man. Such synthetic equivalents are within the definition of "natural origin". It is important to note that in cases where the composition would include a combination of more than one phenolic compound, the combination would not consist of i-carvacrol, thymol and p-cymene or ii-thymol and terpineol together or in combination with other phenolic compounds.

The term "appendage" is intended to mean an external body part, or natural prolongation, that protrudes from an organism's body, such as the arm, hand, leg, foot, hoof, sexual organs, tails, ears, nose, udder, etc.

The term "skin" is intended to mean the soft outer covering of vertebrates. In mammals, the skin is the largest organ of the integumentary system made up of multiple layers of ectodermal tissue, and guards the underlying muscles, bones, ligaments and internal organs. This includes the epidermis, dermis, and hypodermis, and the hair and fur.

The terms "topical" or "topically" are intended to mean the body and body surface of a subject, including the skin and/or mucous membranes, as well as the appendages covered by the skin.

The term "time sufficient" is intended to mean any time necessary to achieve the desired therapeutic or preventive results. For example, the time may be 1, 2, 3, 4, 5, 6, 7, 8, 9, 10, 15, 30, 60 seconds or minutes, or 1.5, 2, 3, 4, 5, 6 or more hours. The time sufficient may also be numerous repetitions of the treatment.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiment there is disclosed a method of reducing a microbial presence on at least one part of a subject. The method includes topically contacting the subject's part with an antimicrobial formulation for a time sufficient to reduce the microbial presence. The antimicrobial formulation includes:

a) at least one antimicrobial isolated or synthetic phenolic compound of natural origin;

b) at least one surfactant sufficient to form a solution or dispersion of the phenolic compound in an aqueous carrier;

c) a solvent for dissolving the phenolic compound; and d) a sufficient aqueous carrier quantity to make 100% (w/w).

Phenolic Compounds of Natural Origin

The phenolic compounds of natural origin used in the present invention are antimicrobial agents that are so-called "natural" antimicrobial actives. These actives derive their names from their natural occurrence in plants. These antimicrobial phenolic compounds are the key chemical components of plant essential oils that have been found to provide the antimicrobial benefit.

The phenolic compounds of natural origin as used in the present invention can be synthetically made by known methods within the capacity of a skilled technician, or can be obtained from plant oil extracts. In an embodiment of the present invention, the phenolic compounds of natural origin are obtained from plant extracts. In a further embodiment of the present invention, the phenolic compounds of natural origin are commercially available.

The phenolic compounds of natural origin as used in the present invention can include, but are not limited to, thymol (present for example in thyme), eugenol (present for example in cinnamon), menthol (present for example in mint), geraniol (present for example in geranium or rose), verbenone (present for example in vervain), eucalyptol (present for example in eucalyptus), cedrol (present for example in cedar), pinocarvone, carvacrol (which is isomeric with thymol, and is present for example in oregano), anethol (present for example in aniseed) hinokitiol, berberine, terpineol, limonene, ratanhiae, citral (present for example in lemon myrtle) and mixtures thereof. According to a preferred embodiment of the present invention the phenolic compounds of natural origin as used in the present invention are thymol, eugenol, carvacrol, and citral. In yet a further preferred embodiment of the present invention, the phenolic compounds of natural origin comprise carvacrol and thymol. In a most preferred embodiment, the phenolic compounds of natural origin comprise thymol. It is important to note that in cases where the composition would include a combination of more than one phenolic compound, the combination would not consist of i-carvacrol, thymol and p-cymene or ii-thymol and terpineol together or in combination with other phenolic compounds.

According to an embodiment, the formulation may comprise from about 0.05% to about 25% (w/w) of the phenolic compound. According to another embodiment, the formulation may comprise from about 5% to about 25% (w/w) of the phenolic compound. According to yet another embodiment, the formulation may comprise from about 15% to about 25% (w/w) of the phenolic compound. According to another embodiment, the formulation may comprise thymol from about 0.05% to about 25% (w/w). According to another embodiment, the formulation may comprise thymol from about 0.05% to about 0.49% (w/w) of the formulation. In a particular embodiment, the antimicrobial formulations of the present invention comprise 0.18% (w/w) thymol. According to yet another embodiment, the formulation may comprise thymol from about 0.23% (w/w) of the formulation.

Essential Oils

In an embodiment, the antimicrobial formulations of the present invention may further comprise one or more essential oils. Essential oils derive their names from their natural occurrence in plants. Essential oils include oils derived from herbs, flowers, trees, and other plants. Such oils are typically present as tiny droplets between the plant's cells, and can be extracted by several methods known to those of skill in the art (e.g., steam distillation, enfleurage (i.e., extraction using fat(s)), maceration, solvent extraction, or mechanical pressing). Essential oils are typically named by the plant or vegetable in which the oil is found. For example, rose oil or peppermint oil is derived from rose or peppermint plants, respectively. Non-limiting examples of essential oils that can be used in the context of the present invention include oils of anise, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea origanum oil, Hydastis carradensis oil, Berberidaceae daceae oil, Ratanhiae and Curcuma longa oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Other essential oils known to those of skill in the art are also contemplated as being useful within the context of the present invention (e.g., International Cosmetic Ingredient Dictionary, 10th edition, 2004, which is incorporated by reference).

According to an embodiment, the essential oil may be essential oil chosen from the origanum oil, thyme oil, and eucalyptus oil. According to a preferred embodiment, the essential oils used in the present invention are enriched in thymol and/or carvacrol. Thymol and carvacrol are naturally occurring disinfectants which are readily degraded in the environment. As such, there is little or no accumulation in the environment or in living organisms, even following repeated application of the antimicrobial formulations of the present invention.

According to an embodiment, the formulation may comprise from about 0.0001% to about 4% (w/w) of the essential oil. According to another embodiment, the formulation may comprise from about 0.01% to about 4% (w/w) of the essential oil. According to yet another embodiment, the formulation may comprise from about 1% to about 4% (w/w) of the essential oil.

Surfactants

A surfactant (surface active agent) is generally intended to refer to a substance which when dissolved in water, or other aqueous system, reduces the surface or interfacial tension between it and another substance or material. According to another embodiment of the present invention the antimicrobial formulations used in the method of the present invention further comprise a surfactant. A suitable surfactant comprises a water soluble or water dispersible nonionic, anionic, cationic, or an amphoteric compound. In a further embodiment, the antimicrobial formulations of the present invention comprise one or more of the conventional anionic surfactants known in the art. A representative listing of surfactants and properties thereof is detailed in Remington's Pharmaceutical Sciences, 17th edition (Mack Publishing Company). Non-limiting examples of surfactants according to an embodiment of the present invention include sodium lauryl sulfate, sorbitan stearate, sorbitan esters, sodium laureth sulfate, sarkosyl, cocamidopropyl betaine (CAPB), sodium lauryl ether sulfonate, alkyl benzene sulfonates, nonylphenol ethoxylate, hexadecylbetaine, lauryl betaine, and ether ethoxylate. According to another embodiment, one or more additional surfactants may be included in the antimicrobial formulations used in the methods of the present invention.

In an embodiment of the present invention, the surfactant aids in the dispersion or emulsification of the phenolic compounds and/or the essential oils used in the present invention, within the aqueous carrier. In a further embodiment of the present invention, the surfactants aids in braking down the structure of biofilms through denaturation. In yet a further embodiment of the present invention, the surfactant allows for the creation of a "foaming effect" when the antimicrobial solution is applied to a topical surface to be treated. In yet a further embodiment of the present invention, the surfactant allows for an improvement of the viscosity response of another surfactant. The creation of a foam allows for the antimicrobial solutions to remain in contact with the topical surface to be treated for longer periods of time. In yet a further embodiment, the surfactant acts as a "wetting" agent. Wetting agents typically reduce the surface tension of the water molecules, allowing for a greater spreading of the solution and a deeper penetration into small crack and crevices of the surface to be treated.

According to an embodiment, the formulation may comprise from about 0.1% to about 15% (w/w) of the surfactant. According to another embodiment, formulation may comprise from about 5% to about 15% (w/w) of the surfactant. According to another embodiment, the formulation comprises from about 10% to about 15% (w/w) of the surfactant.

Solvents

The phenolic compounds of natural origin as used in the present invention (e.g. carvacrol, thymol) are typically not sufficiently soluble in an aqueous medium. The antimicrobial formulations used in the present invention thus typically comprise a solvent. The solvents may be hydrophilic, hydrophobic or amphiphilic in nature. In an embodiment, the antimicrobial formulations of the present invention comprise an amphiphilic solvent. Amphiphilic solvents are capable of solubilizing the phenolic compounds of natural origin and/or the essential oil(s) in the aqueous carrier. Non-limiting examples of solvents according to an embodiment of the present invention include methanol, ethanol, hexadecane, propylene glycol, propylene glycol n-butyl ether, propylene glycol methyl ether acetate, propylene glycol methyl ether, dipropylene glycol n-propyl ether, ethylene glycol methyl ether, 1,3-propanediol and hexylene glycol. The addition of a significant amount of solvent to the antimicrobial solutions of the present invention, allows for the solutions to be used at temperatures slightly inferior to 0° C. It is well within the capacity of a skilled technician to determine such amounts of solvent. According to an embodiment of the present invention, the preferred solvent is propylene glycol methyl ether.

According to an embodiment, the formulation may comprise from about 0.1% to about 40% (w/w) of the solvent. According to another embodiment, the formulation may comprise from about 5% to about 35% (w/w) of the solvent. According to yet another embodiment, the formulation may comprise from about 15% to about 30% (w/w) of the solvent.

Sequestering Agents

According to yet another embodiment, the antimicrobial formulations used in the method of the present invention are often prepared on site from mixtures of ingredients in concentrated solution. According to an embodiment, tap water is used for dilution. Tap water generally has a certain amount of hardness. Since the presence of dissolved minerals (e.g. $Ca^{++}$, $Mg^{++}$) may adversely affect the performance and properties of the antimicrobial formulation, a sequestering agent is included in the formulation to chelate the dissolved minerals in the form of a water soluble complex. Sequestering agents are well known in the art. Non-limiting examples include ethylene diamine tetraacetic acid (EDTA) sodium salt, sodium gluconate, sodium citrate, trisodium ethylenediamine disuccinate, citric acid, trisodium NTA, sodium phosphate and sodium choleate. Sequestering agents typically prevent the dissolved minerals from binding to the surfactant molecules. Moreover, sequestering agents may remove minerals from the surface to be disinfected.

According to an embodiment, the formulation may comprise from about 0.01% to about 10% (w/w) of the sequestering agent. According to another embodiment, the formulation may comprise from about 1% to about 5% (w/w) of the sequestering agent. According to yet another embodiment, the formulation may comprise from about 1% to about 3% (w/w) of the sequestering agent.

Fragrance

Phenolic compounds of natural origin as used in the present invention typically have an associated pungent odor which may impede large-scale applications. Thus, according to yet another embodiment, the antimicrobial formulations of the present invention may further comprise one or more agents having the function of imparting a more pleasant odor thereto. According to yet another embodiment, the agent may have the dual function of further enhancing the antimicrobial properties of the formulations used in the present invention while imparting a more pleasant odor thereto. Non-limiting examples of agents imparting a pleasant odor and/or enhancing the antimicrobial properties comprise carvacrol, cymene, cineol, eugenol, thymol, menthol, citral and limonene.

According to an embodiment, the formulation may comprise from about 0.01% to about 5% (w/w) of the fragrance. According to yet another embodiment, the formulation may comprise from about 0.03% to about 5% (w/w) of the fragrance. According to yet another embodiment, the formulation may comprise from about 0.5% to about 5% (w/w) of the fragrance. According to yet another embodiment, the formulation may comprise from about 0.01% to about 0.15% (w/w) of the fragrance.

Other Ingredients

The antimicrobial formulations of the present invention may optionally include a wide range of additional ingredients non-limiting examples of which include colorants, thickening agents, aloe vera, glycerine, vitamins and pH adjusting agents. Such additional ingredients are within the capacity of a skilled technician. Preferably, the pH of the antimicrobial formulation may be from about 1 to about 10.

The colorant may be a dye, a pigment, a biological pigment, an ink, a food coloring. In embodiments, the colorant may help identifying a surface as having been treated with the composition of the present invention. Examples of colorants include but are not limited to FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 3—Erythrosine, E127 (pink shade, commonly used in glace cherries); FD&C Red No. 40—Allura Red AC, E129 (red shade); FD&C Yellow No. 5—Tartrazine, E102 (yellow shade); FD&C Yellow No. 6—Sunset Yellow FCF, E110 (orange shade); E104: Quinoline Yellow; E122: Carmoisine; E124: Ponceau 4R; E131: Patent Blue V; E142: Green S; Annatto (E160b), a reddish-orange dye made from the seed of the achiote; Betanin (E162) extracted from beets; Butterfly pea, a blue food dye; Caramel coloring (E150a-d), made from caramelized sugar; Chlorophyllin (E140), a green dye made from chlorella algae; Elderberry juice; Lycopene (E160d); Carmine (E120), a red dye derived from the cochineal insect, *Dactylopius coccus*; Pandan (*Pandanus amaryllifolius*), a green food coloring; Paprika (E160c), Turmeric (curcuminoids, E100), Saffron (carotenoids, E160a). Preferably the dye is blue.

The colorant may be used in any suitable concentration, for example at concentrations of about 0.00005% to about 15% w/w, or from about 0.0005% to about 15% w/w, or from about 0.005% to about 15% w/w, or from about 0.05% to about 15% w/w, or from about 0.01% to about 15% w/w, or from about 0.1 to about 15% w/w, or from about 0.25 to about 15% w/w, or from about 0.5% to about 15% w/w, or from about 1% to about 15%, or from about 5% to about 15%, or from about 10% to about 15%, about 0.00005% to about 10% w/w, or from about 0.0005% to about 10% w/w, or from about 0.005% to about 10% w/w, or from about 0.05% to about 10% w/w, or from about 0.01% to about 10% w/w, or from about 0.1 to about 10% w/w, or from about 0.25 to about 10% w/w, or from about 0.5% to about 10% w/w, or from about 1% to about 10%, or from about 5% to about 10%, about 0.00005% to about 5% w/w, or from about 0.0005% to about 5% w/w, or from about 0.005% to about 5% w/w, or from about 0.01% to about 5% w/w, or from about 0.05% to about 5% w/w, or from about 0.1 to about 5% w/w, or from about 0.25 to about 5% w/w, or from about 0.5% to about 5% w/w, or from about 1% to about 5%, about 0.00005% to about 1% w/w, or from about 0.0005% to about 1% w/w, or from about 0.005% to about 1% w/w, or from about 0.01% to about 1% w/w, or from about 0.1 to about 1% w/w, or from about 0.25 to about 1% w/w, or from about 0.5% to about 1% w/w, about 0.00005% to about 0.25% w/w, or from about 0.0005% to about 0.25% w/w, or from about 0.005% to about 0.25% w/w, or from about 0.01% to about 0.25% w/w, or from about 0.1 to about 0.25% w/w, or about 0.00005% to about 0.1% w/w, or from about 0.0005% to about 0.1% w/w, or from about 0.005% to about 0.1% w/w, or from about 0.01% to about 0.1% w/w, or about 0.00005% to about 0.1% w/w, or from about 0.0005% to about 0.1% w/w, or from about 0.005% to about 0.1% w/w, or from about 0.01% to about 0.1% w/w, or about 0.00005% to about 0.01% w/w, or from about 0.0005% to about 0.01% w/w, or from about 0.005% to about 0.01% w/w, or from about 0.00005% to about 0.005% w/w, or from about 0.0005% to about 0.005% w/w.

As used herein, the term "pH adjusting agent" is intended to mean a compound that will change the pH of a solution of the present invention by making it more alkaline or acidic, as may be required. Examples include acids, bases, as well as buffering agents.

According to some embodiments, in the first stage of cleaning, the identity of the pollutant to be removed needs to be ascertained. There are two basic categories for pollutants: organic and inorganic. Organic pollutants are those based on carbon, such as oils, fats, carbohydrates, proteins, molds, yeasts, and animal waste. Inorganic pollutants are substances that are not organic (carbon-based), such as deposits of tartar and lime, rust, corrosion and oxidation. These types of fouling are usually removed by an acid cleaner (pH <7). The cleaning efficacy can be impacted by the pH of the solution. Furthermore, animal skins have defined pH and they get in contact with solutions having pH levels that are divergent from these defined pH, which can cause irritation and impair healing. Therefore, when animal skins are in contact with a solution of a similar pH value, the contact is gentler, causing no or less irritation and favors healing. Therefore, the pH of the formulations of the present invention may be from about 1 to about 11, or from about 2 to about 11, or from about 3 to about 11, or from about 4 to about 11, or from about 5 to about 11, or from about 6 to about 11, or from about 7 to about 11, or from about 8 to about 11, or from about 9 to about 11, or from about 10 to about 11, or from about 1 to about 10, or from about 2 to about 10, or from about 3 to about 10, or from about 4 to about 10, or from about 5 to about 10, or from about 6 to about 10, or from about 7 to about 10, or from about 8 to about 10, or from about 9 to about 10, or from about 1 to about 9, or from about 2 to about 9, or from about 3 to about 9, or from about 4 to about 9, or from about 5 to about 9, or from about 6 to about 10, or from about 7 to about 9, or from about 8 to about 9, or from about 1 to about 8, or from about 2 to about 8, or from about 3 to about 8, or from about 4 to about 8, or from about 5 to about 8, or from about 6 to about 8, or from about 7 to about 8, or from about 1 to about 7, or from about 2 to about 7, or from about 3 to about 7, or from about 4 to about 7, or from about 5 to about 7, or from about 6 to about 7, or from about 1 to about 6, or from about 2 to about 6, or from about 3 to about 6, or from about 4 to about 6, or from about 5 to about 6, or from about 1 to about 5, or from about 2 to about 5, or from about 3 to about 5, or from about 4 to about 5, or from about 1 to about 4, or from about 2 to about 4, or from about 3 to about 4, or from about 1 to about 3, or from about 2 to about 3, or from about 1 to about 2, or about 1, or about 1.5, or about 2, or about 2.5, or about 3, or about 3.5, or about 4, or about 4.5, or about 5, or about 5.5, or about 6, or about 6.5, or about 7, or about 7.5, or about 8, or about 8.5, or about 9, or about 9.5, or about 10, or about 10.5, or about 11.

According to an embodiment, the pH adjusting agent is chosen from citric acid, lactic acid, hydrochloric acid, boric acid, acetic acid, sodium hydroxide, potassium hydroxide, sulfuric acid, calcium carbonate ($CaCO_3$), ammonium carbonate, ammonium bicarbonate, ammonium citrate, sodium citrate, magnesium carbonate, sodium carbonate, mono, di and/or trisodium phosphate, mono, di and/or tripotassium phosphate, Tris(hydroxymethyl) aminomethane (TRIS), paracetic acid, propionic acid, fumaric acid, sorbic acid, benzoic acid, phenylacetic acid, malic acid, tartaric acid, dehydroacetic acid, amino acids and zwitterions, such as glycine, 2-amino-2methyl-1,3-propanediol (AMPD), N-(1, 1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N, N-bis[2-hydroxyethyl]-2-aminoethanesulphonic acid (BES), (2-[2-hydroxy-1,1-bis(hydroxymethyl) ethylamino] ethanesulphonic acid) (TES), 2-(N-morpholino)ethanesulfonic acid (MES), N-[Tris(hydroxymethyl)methyl]glycine (Tricine); N-Tris(hydroxymethyl)methyl-3-aminopropanesulfonic acid (TAPS) and 3-N-Morpholino propanesulfonic acid (MOPS), piperazie-N, N'-bis[2-hydroxypropanesulphonic] acid (POPSO), and combinations thereof. According to a preferred embodiment, the pH adjusting agent is citric acid. According to another preferred embodiment, the pH adjusting agent is lactic acid.

The role of the pH adjusting agent is to adjust the acidity or alkalinity of the composition of the present invention, or increase the buffer capacity in order to reduce pH variation upon application. According to an embodiment, the composition of the present invention may comprise from about 0.01% to about 5% (w/w), or from about 0.01% to about 4%, or from about 0.01% to about 3%, or from about 0.01% to about 2%, or from about 0.01% to about 1%, or from about 0.01% to about 0.75%, or from about 0.01% to about 0.5%, or from about 0.01% to about 0.25%, or from about 0.01% to about 0.1%, or from about 0.01% to about 0.075%, or from about 0.01% to about 0.05%, or from about 0.01% to about 0.025%, or from about 0.01% to about 0.02%, or from about 0.01% to about 0.015%, or 0.015% to about 5% (w/w), or from about 0.015% to about 4%, or from about 0.015% to about 3%, or from about 0.015% to about 2%, or from about 0.015% to about 1%, or from about 0.015% to about 0.75%, or from about 0.015% to about 0.5%, or from about 0.015% to about 0.25%, or from about 0.015% to about 0.1%, or from about 0.015% to about 0.075%, or from about 0.015% to about 0.05%, or from about 0.015% to about 0.025%, or from about 0.015% to about 0.02%, or 0.02% to about 5% (w/w), or from about 0.02% to about 4%, or from about 0.02% to about 3%, or from about 0.02% to about 2%, or from about 0.02% to about 1%, or from about 0.02% to about 0.75%, or from about 0.02% to about 0.5%, or from about 0.02% to about 0.25%, or from about 0.02% to about 0.1%, or from about 0.02% to about 0.075%, or from about 0.02% to about 0.05%, or from about 0.02% to about 0.025%, or 0.025% to about 5% (w/w), or from about 0.025% to about 4%, or from about 0.025% to about 3%, or from about 0.025% to about 2%, or from about 0.025% to about 1%, or from about 0.025% to about 0.75%, or from about 0.025% to about 0.5%, or from about 0.025% to about 0.25%, or from about 0.025% to about 0.1%, or from about 0.025% to about 0.075%, or from about 0.025% to about 0.05%, or 0.05% to about 5% (w/w), or from about 0.05% to about 4%, or from about 0.05% to about 3%, or from about 0.05% to about 2%, or from about 0.05% to about 1%, or from about 0.05% to about 0.75%, or from about 0.05% to about 0.5%, or from about 0.05% to about 0.25%, or from about 0.05% to about 0.1%, or from about 0.05% to about 0.075%, or 0.075% to about 5% (w/w), or from about 0.075% to about 4%, or from about 0.075% to about 3%, or from about 0.075% to about 2%, or from about 0.075% to about 1%, or from about 0.075% to about 0.75%, or from about 0.075% to about 0.5%, or from about 0.075% to about 0.25%, or from about 0.075% to about 0.1%, or 0.1% to about 5% (w/w), or from about 0.1% to about 4%, or from about 0.1% to about 3%, or from about 0.1% to about 2%, or from about 0.1% to about 1%, or from about 0.1% to about 0.75%, or from about 0.1% to about 0.5%, or from about 0.1% to about 0.25%, or 0.25% to about 5% (w/w), or from about 0.25% to about 4%, or from about 0.25% to about 3%, or from about 0.25% to about 2%, or from about 0.25% to about 1%, or from about 0.25% to about 0.75%, or from about 0.25% to about 0.5%, or 0.5% to about 5% (w/w), or from about 0.5% to about 4%, or from about 0.5% to about 3%, or from about 0.5% to about 2%, or from about 0.5% to about 1%, or from about 0.5% to about 0.75%, or 0.75% to about 5% (w/w), or from about 0.75% to about 4%, or from about 0.75% to about 3%, or from about 0.75% to about 2%, or from about 0.75% to about 1%, or 1% to about 5% (w/w), or from about 1% to about 4%, or from about 1% to about 3%, or from about 1% to about 2%, or 2% to about 5% (w/w), or from about 2% to about 4%, or from about 2% to about 3%, or 3% to about 5% (w/w), or from about 3% to about 4%, or 4% to about 5% (w/w) of a pH adjusting agent. The preferred range over which it may be used is from about 1% to about 5% (w/w) in concentrated form of the present invention, or about 0.01% to about 0.05% (w/w).

Method of Disinfection

According to an embodiment of the present invention, the antimicrobial formulations of the present invention may be applied onto a subject's part to be topically contacted by means of a variety of techniques. In an embodiment, the antimicrobial formulations of the present invention are applied using a diffuser or a mist blower. Alternatively, the antimicrobial formulations of the present invention can also be formulated into aerosol formulations. Further means of applying the antimicrobial solutions of the present invention are within the capacity of a skilled technician. For example, the contact may be by means of a bath, a footbath, a direct application, a wipe, a cream, an ointment, an unguent. Preferably, the topical contact may be with a footbath.

The antimicrobial formulations of the present invention can either be applied directly or can be diluted prior to application. Due to the substantially non-corrosive nature of the antimicrobial formulations of the present invention, the formulations can be readily applied without undue damage to the subject's part. Non limiting example of a subject's part that may be treated according to the method of the present invention include a skin, a limb, a head, an ear, a nose, a hand, a foot, a mucosa, a hoof, or combinations thereof.

According to an embodiment, the subject to be contacted according to the method of the present invention may be a mammal or poultry. According to embodiments, the mammal may be chosen from a bovine, an ovine, a canine, a caprine, an equine, a feline, a porcine, a rodent and a human. According to embodiments, the poultry is chosen from a chicken, a duck, an emu, a goose, a turkey, and a pheasant.

According to yet another embodiment, the method of the present invention may be used for reducing a microbial presence for preventing or treating a disease such as a hoof rot, hoof scald, hoof abscesses, and combinations thereof. According to yet another embodiment, the method of the present invention may be used for preventing or treating a disease chosen from a skin lesion, a disease of an appendage, a bacterial infection, and a fungal infection.

According to an embodiment, the bacterial infection may be one of a *salmonella* infection, an *E. Coli* infection, a staphylococcal infection, a spirochete infection, an impetigo, an ecthyma, a carbunculosis, a folliculitis, an erysipelas, an *aeromonas* infection, an african tick bite fever, an american tick bite fever, an *arcanobacterium haemolyticum* infection, a bacillary angiomatosis, a bejel, a blastomycosis-like pyoderma, a blistering distal dactylitis, a botryomycosis, a Brill-Zinsser disease, a brucellosis, a bullous impetigo, a canker, a cat scratch disease, a chancre, a chancroid, a chlamydial infection, a chronic lymphangitis, a chronic recurrent erysipelas, a chronic undermining burrowing ulcers, a chromobacteriosis infection, a condylomata lata, a cutaneous actinomycosis, a cutaneous anthrax infection, a cutaneous diphtheria infection, a cutaneous group B streptococcal infection, a cutaneous *pasteurella* hemolytica infection, a cutaneous streptococcus iniae infection, a dermatitis gangrenosa, a desert sore, a digital dermatitis, a ecthyma gangrenosum, a ehrlichiosis ewingii infection, a elephantiasis nostras, a endemic typhus, a epidemic typhus, a erysipelas, a erysipeloid of rosenbach, a erythema marginatum, a erythrasma, a external otitis, a felon, a flea-borne spotted fever, a flinders island spotted fever, a flying squirrel typhus, a folliculitis, a foot abscess, a Fournier gangrene, a furunculosis, a gas gangrene, a glanders, a Glässer's disease, a gonococcemia, a gonorrhea, a gram-negative folliculitis, a gram-negative toe web infection, a granuloma inguinale, a green nail syndrome, a group jk corynebacterium sepsis, a haemophilus influenzae cellulitis, a *helicobacter* cellulitis, a hospital furunculosis, a hot tub folliculitis, a human granulocytotropic anaplasmosis, a human monocytotropic ehrlichiosis, an impetigo contagiosa, an infected oil gland, an interdigital dermatitis, an interdigital phlegmon, an Italian foot rot a japanese spotted fever, a joint-ill, a leptospirosis, a *Listeria monocytogenes* infection, a listeriosis, a Ludwig's angina, a lupoid sycosis, a lyme disease, a lymphogranuloma venereum, a malakoplakia, a mediterranean spotted fever, a melioidosis, a meningococcemia, a missouri lyme disease, a *mycoplasma* infection, a necrotizing fasciitis, a neonatal toxic shock-like exanthematous disease, a nocardiosis, a noma neonatorum, a north asian tick typhus, an ophthalmia neonatorum, an erysipelas, an oroya fever, a pasteurellosis, a periapical abscess, a pinta, a pitted keratolysis, a plague, a pododermatitis, a primary gonococcal dermatitis, a pseudomonal pyoderma, a pseudomonas hot-foot syndrome, a pyogenic paronychia, a pyomyositis, a Q fever, a Queensland tick typhus, a rat-bite fever, a recurrent toxin-mediated perineal erythema, a rhinoscleroma, a *rickettsia aeschlimannii* infection, a rickettsialpox, a ringbone, a rocky mountain spotted fever, a saber shin, a saddle nose, a salmonellosis, a scarlet fever, a scrub typhus, a shigellosis, a staphylococcal scalded skin syndrome, a streptococcal intertrigo, a super foot rot, a superficial pustular folliculitis, a sycosis vulgaris, a syphilid, a syphilis, a thrush, a tick-borne lymphadenopathy, a toxic shock syndrome, a trench fever, a tropical ulcer, a tularemia, a verruga peruana, a *vibrio vulnificus* infection, or a yaws.

According to an embodiment, the fungal infection may be one of a aspergillus infection, a cryptococcosis, a ringworm, a candidiasis, a psoriasis, a thrush, a blastomycosis, a chytridiomycosis, a coccidioidomycosis, a histoplasmosis, a tinea (pityriasis) versicolor, an african histoplasmosis, an alternariosis, an antibiotic candidiasis, a black piedra, a candidal intertrigo, a candidal onychomycosis, a candidal paronychia, a candidal vulvovaginitis, a candidid, a chromoblastomycosis, a chronic mucocutaneous candidiasis, a coccidioidomycosis, a congenital cutaneous candidiasis, a cryptococcosis, a dermatophytid, a diaper candidiasis, a disseminated coccidioidomycosis, a distal subungual onychomycosis, an entomophthoromycosis, an erosio interdigitalis blastomycetica, a favus, a fungal folliculitis, a fusariosis, a geotrichosis, a granuloma gluteale infantum, a histoplasmosis, a hyalohyphomycosis, a kerion, a lobomycosis, a mucormycosis, a mycetoma, a north american blastomycosis, an onychomycosis, an oral candidiasis, an otomycosis, a perianal candidiasis, a perlèche, a phaeohyphomycosis, a piedra, a pityrosporum folliculitis, a primary cutaneous aspergillosis, a primary cutaneous coccidioidomycosis, a primary cutaneous histoplasmosis, a primary pulmonary coccidioidomycosis, a primary pulmonary histoplasmosis, a progressive disseminated histoplasmosis, a proximal subungual onychomycosis, a rhinosporidiosis, a south american blastomycosis, a sporotrichosis, a systemic candidiasis, a tinea barbae, a tinea capitis, a tinea corporis, a tinea corporis gladiatorum, a tinea cruris, a tinea faciei, a tinea imbricata, a tinea incognito, a tinea manuum, a tinea nigra, a tinea pedis, a tinea versicolor, a white piedra, a white superficial onychomycosis, or a zygomycosis.

According to an embodiment, the skin lesion may be one of an ulcer, a diabetic ulcer, a furuncle, a carbuncle, a fissure, a crack, or a blister.

According to an embodiment, the disease of an appendage may be a mastitis.

Formulations of the present invention can include any number of combinations of ingredients discussed throughout this specification (e.g., phenolic compounds of natural origin, essential oils, surfactants, solvents, sequestering agents, water, etc.). It is also contemplated that that the concentrations of the ingredients can vary.

The present invention will be more readily understood by referring to the following examples which are given to illustrate the invention rather than to limit its scope.

EXAMPLE 1

Antimicrobial Formulations

TABLE 1

| | Antimicrobial formulations | | | | | | |
|---|---|---|---|---|---|---|---|
| | Thymol Crystal (% w/w) | Essential Oil (% w/w) | Sequestering agent (% w/w) | Surfactant(s) (% w/w) | Solvent (% w/w) | Fragrance (% w/w) | pH |
| A | 0.18 | 0.03 | 0.01 | 0.12 | — | 0.01 | 6.9 |
| B | 0.18 | 0.03 | 0.01 | — | 0.18 | 0.01 | 6.7 |
| C | 0.18 | 0.03 | — | 0.12 | 0.18 | 0.01 | 6.5 |
| 1 | 0.18 | 0.03 | 0.01 | 0.12 | 0.18 | 0.01 | 6.5 |
| D | 18 | 3 | 1 | 12 | — | 1 | 8.1 |
| E | 18 | 3 | 1 | — | 18 | 1 | 7.9 |
| 2 | 18 | 3 | 1 | 12 | 18 | 1 | 8.8 |
| 3 | 0.18 | 0.03 | 0.09 | 0.12 | 0.76 | — | 8.0 |
| 4 | 6 | 1 | 3 | 4 | 25 | — | 8.2 |
| 5 | 23 | — | — | 12 | 36 | 3 | 9.73 |
| 6 | 0.23 | — | — | 0.12 | 0.36 | 0.03 | 7.31 |
| 7 | 8 | — | 3 | 12 | 30 | 3 | 9.58 |
| 8 | 0.24 | — | 0.09 | 0.36 | 0.9 | 0.09 | 7.57 |
| 9 | 0.24 | — | — | 0.5 | 5 | 0.09 | 7.6 |

TABLE 1-continued

Antimicrobial formulations

| | Solubility in Water/Stability | Foaming Effect | Foaming Effect in Hard Water |
|---|---|---|---|
| A | NO | YES | YES |
| B | NO | NO | YES |
| C | YES | YES | NO |
| 1 | YES | YES | YES |
| D | NO | YES | n/a |
| E | NO | NO | n/a |
| 2 | YES | YES | n/a |
| 3 | YES | YES | YES |
| 4 | YES | YES | n/a | n/a: Not applicable this formula requires dilution before use

When a sequestering agent such as sodium citrate is present, it is first dissolved in a predetermined amount of water and stirred until dissolution. Glycol ether PM or 1,3-propanediol (solvent), thymol, essential oil (origanum oil) and optionally a fragrance are then added and stirred until dissolution. Surfactants (Sodium Lauryl Sulfate and/or Sodium Laureth Sulfate and/or Cetyl Betaine) and additional water are then added and stirred until dissolution to provide a 100% (w/w) formulation. The final formulation is stirred until a homogeneous solution is obtained. Formulation 1, obtained from Formulation 2 by means of dilution with water (1% w/w), is considered a "ready to use" formulation. Formulation 3, obtained from Formulation 4 by means of dilution with water (3% w/w), is considered a "ready to use" formulation. Formulation 6, obtained from Formulation 5 by means of dilution with water (1% w/w), is considered a "ready to use" formulation. Formulation 8, obtained from Formulation 7 by means of dilution with water (3% w/w), is considered a "ready to use" formulation. Formulation 9 is a ready to use formulation.

As illustrated hereinabove, the formulations are first formulated as a "concentrate" (Formulations 2, 4, 5 and 7), dilution of which provides for the preparation of Formulations 1, 3, 6 and 8. Formulations A, B, C, D, E, 1 and 2 comprise essential oil (Origanum Oil). Formulations 3 and 4 do not comprise any fragrance. Formulations 5,6,7,8, and 9 can comprise a fragrance. Formulations 5,6 and 9 do not comprise any sequestering agent. The formulations have a pH ranging from about 6.5 to about 9.7.

As illustrated herein above, Formulation A and D have no solvent and are neither stable nor soluble in water. The solvent helps for solubility and stability of the Formulations 1, 2, 3, 4, 5, 6, 7, 8 and 9. Formulation B and E have no surfactant and are not stable, not soluble in water, and have no foaming effect. Surfactant(s) help for the stability, solubility and foaming effect of Formulations 1, 2, 3, 4, 5, 6, 7, 8 and 9. Formulation C has a solvent and surfactant, and is stable, soluble in water and has a foaming effect. Dilution using hard water did not affect the characteristics of Formulations 1, 3 and 8 which is indicative of the efficacy of the sequestering agent for Formulations 1,3 and 8.

EXAMPLE 2

Sequestering Agent

Foaming capacity is a very important characteristic of disinfectants. It is crucial that disinfectants foam even when formulated of diluted with hard water. This is especially important in rural setting, where the water used to dilute agricultural disinfectant will almost always be hard water.

Formulations 10 to 17 (Table 2) were prepared using 400 ppm hard water. 20 mL of formulations 10 to 17 were dispensed in cylindrical graduated cylinders. The cylinders were shaken for 10 seconds, and then left to stand for 1 minute. Foam height and thickness were then measured for each formulation (Table 3). The test was repeated 2 other times, for a total of 3 measurements for each formulation.

TABLE 2

Formulations with hard water

| | Formulation | | | | | | | |
|---|---|---|---|---|---|---|---|---|
| | 10 | 11 | 12 | 13 | 14 | 15 | 16 | 17 |
| Thymol % | 0.23 | 0.23 | 0.23 | 0.23 | 0.23 | 0.23 | 0.23 | 0.23 |
| Surfactant % | 0.35 | 0.35 | 0.35 | 0.35 | 0.35 | 0.35 | 0.35 | 0.35 |
| Solvent % | 0.9 | 0.9 | 0.9 | 0.9 | 0.9 | 0.9 | 0.9 | 0.9 |
| Essential Oil % | 0 | 0.02 | 0 | 0.02 | 0 | 0.02 | 0 | 0.02 |
| Fragrance % | 0 | 0 | 0.03 | 0.03 | 0 | 0 | 0.03 | 0.03 |
| Sequestering agent % | 0.09 | 0.09 | 0.09 | 0.09 | 0 | 0 | 0 | 0 |
| Hard Water % | Q.S. | Q.S. | Q.S. | Q.S. | Q.S. | Q.S. | Q.S. | Q.S. |

Q.S. stands for quantity sufficient or to add enough of the major ingredient until a total of 100% of the formula is reached.

TABLE 3

Foam height (cm) and thickness after 1 minute, when using standard AOAC 400 ppm hard water

| | Formulation | | | | | | | |
|---|---|---|---|---|---|---|---|---|
| | 10 | 11 | 12 | 13 | 14 | 15 | 16 | 17 |
| Foam height | 13 | 10 | 19 | 12 | 11 | 9 | 13 | 13 |
| | 10 | 14 | 18 | 13 | 13 | 9 | 13 | 10 |
| | 10 | 13 | 14 | 13 | 10 | 8 | 10 | 10 |
| Thickness | 3 | 3 | 2 | 2 | 3 | 3 | 3 | 2 |
| | 3 | 3 | 2 | 3 | 3 | 2 | 3 | 2 |
| | 3 | 3 | 2 | 3 | 2 | 2 | 2 | 2 |

Foam thickness: 1 = thin, bubble bath like; 5 = thick, shaving cream like

As illustrated herein above, Foam thickness was higher for Formulations 10, 11, 12 and 13 containing a sequestring agent (2.75) than Formulations 14, 15, 16 and 17 not containing a sequestring agent (2.42), a difference of 14%. Foam height was significatively higher ($p<0.05$, unpaired t-test) for formulations containing a sequestring agent (13.75 cm) when compared to formulations not containing a sequestring agent (10.75 cm), a difference of 23%. The results clearly indicate that the presence of a sequestring agent affects the quantity of foam yielded by a formulation.

The importance of foam in disinfecting applications in very important, especially in agricultural settings.

EXAMPLE 3

Biological Efficacy of Selected Phenolic Compounds and Essential Oils

The minimum concentration at which a total antimicrobial activity could be observed is determined for selected phenolic compounds of natural origin and selected essential oils using the AOAC method 955.15 ("Phenol Coefficient Method") with minor modifications. Different concentrations of essential oils and phenolic compounds of natural origin are incorporated into formulation F (see table hereinbelow) and inoculated with a 0.05% bacterial suspension of *Staphylococcus aureus* (ATCC 6538; concentration of about 8 logs). After a contact time of 10 minutes, 0.1 ml of the inoculated solution is transferred to a broth culture with neutralizing (Difco 268110) and incubated over a period of 72 hours at 37° C. The presence of turbidity in the broth culture is indicative of the survival of the microorganism As illustrated herein below in Table 4, the results are indicative of the excellent antimicrobial activity of both thymol and carvacrol. Thymol and carvacrol need a much lower concentration (0.07% v/v) to achieve total antimicrobial activity than other phenolic compounds and essential oils.

TABLE 4

Minimal concentration of antimicrobial agents

| Antimicrobial Agent | Minimal Concentration (v/v %) |
|---|---|
| Thymol | 0.07 |
| Carvacrol | 0.07 |
| Eugenol | 0.4 |
| Citral | >1% |
| Thyme oil | 0.3 |
| *Origanum* oil | 0.2 |
| *Eucalyptus* oil | >1% |
| Lemon oil | >1% |

EXAMPLE 4

Quantitative Microbial Reduction Assay

The antimicrobial activity for selected formulations of the present invention is determined. The different formulations (Table 5) are inoculated with 0.05% of a bacterial culture of *Staphylococcus aureus* (ATCC 6538) freshly incubated over a period of 48 hours at 37° C. in an optimal growth medium. After a contact time of 10 minutes, 0.1 ml of the inoculated solution is seeded at different dilutions on TSA agar (Difco 255320) with neutralizing to determine the residual microbial load. The log reduction is determined by calculating the logarithm of the residual charge obtained with the reference formulation (i.e. water) and comparing it with the residual charge obtained using any of the formulations comprising either a phenolic compound or an essential oil.

Several formulations comprising a phenolic compound of natural origin or an essential oil (0.18%) are tested to determine their effectiveness in reducing the load of *Staphylococcus aureus* (ATCC 6538). The solutions are prepared from a concentrate and diluted with water (1:100). As illustrated herein below in Table 5, the results are indicative of the high efficiency of Formulations 10, 11 and 12 in reducing the load of *Staphylococcus aureus*.

TABLE 5

Microbial reduction

| | Antimicrobial Agent (w/w) | Sequestring agent (w/w) | Surfactant (w/w) | Solvent (w/w) | Log Reduction |
|---|---|---|---|---|---|
| F | — | 0.01 | 0.12 | 0.18 | 0.60 |
| 10 | Thymol | 0.01 | 0.12 | 0.18 | 7.63 |
| 11 | Carvacrol | 0.01 | 0.12 | 0.18 | 7.63 |
| G | Eugenol | 0.01 | 0.12 | 0.18 | 2.50 |
| H | Citral | 0.01 | 0.12 | 0.18 | 2.04 |
| I | Thyme oil | 0.01 | 0.12 | 0.18 | 3.06 |
| 12 | *Origanum* oil | 0.01 | 0.12 | 0.18 | 7.63 |
| J | *Eucalyptus* oil | 0.01 | 0.12 | 0.18 | 0.71 |
| K | Lemon oil | 0.01 | 0.12 | 0.18 | 0.64 |

EXAMPLE 5

Biological Efficacy of Individual Ingredients

Formulations 8 and 13 to 25 are prepared with individual ingredients and combinations of ingredients of the formulations of the present invention (Table 6). Formulations Formulations 8 and 13 to 25 are then tested for their biological efficacy against *Staphylococcus aureus*. Briefly, 0.1 mL of bacterial culture containing $1 \times 10^8$ CFU of *Staphylococcus aureus* (i.e. 100 000 000 bacteria) is inoculated in a tube containing 10 mL of a given formulation (diluted at a given ratio). The tube's content is then mixed and let stand for 2 minutes (the "contact time"). After 2 minutes, 0.01 mL of tube content is transferred to a tube containing 9 mL of a neutralizing bacterial culture media (Letheen Broth) that stops the antimicrobial action of the formulation and allows microbial growth. Tubes are then checked for presence of microbial growth after 72 h. The more potent the antimicrobial effect of the formulation, the more it can be diluted before it is no longer potent enough to kill at least 99.999% (5 logs) of the bacteria during the given contact time.

TABLE 6

Formulations with individual or combined ingredients

| | Formulation | | | | | | | | | |
|---|---|---|---|---|---|---|---|---|---|---|
| | 13 | 14 | 15 | 16 | 17 | 18 | 19 | 20 | 21 | 22 |
| Thymol % (w/w) | 0.24 | 0 | 0 | 0.24 | 0.24 | 0 | 0 | 0 | 0 | 0 |
| Surfactant % (w/w) | 0 | 0.36 | 0 | 0.36 | 0 | 0.36 | 0 | 0 | 0 | 0 |
| Solvent % (w/w) | 0 | 0 | 0.9 | 0 | 0.9 | 0.9 | 0 | 0 | 0 | 0 |
| Essential Oil (w/w) | 0 | 0 | 0 | 0 | 0 | 0 | 0 | 0.02 | 0 | 0.02 |
| Fragrance (w/w) | 0 | 0 | 0 | 0 | 0 | 0 | 0 | 0 | 0.03 | 0.03 |

TABLE 6-continued

| Formulations with individual or combined ingredients | | | | | | | | | | |
|---|---|---|---|---|---|---|---|---|---|---|
| Sequestring agent (w/w) | 0 | 0 | 0 | 0 | 0 | 0 | 0.09 | 0 | 0 | 0.09 |
| Water % (w/w) | Q.S. | Q.S. | Q.S. | Q.S. | Q.S. | Q.S. | Q.S | Q.S. | Q.S. | Q.S. |

| | Formulation | | | |
|---|---|---|---|---|
| | 23 | 24 | 8 | 25 |
| Thymol % (w/w) | 0.24 | 0.24 | 0.24 | 0.24 |
| Surfactant % (w/w) | 0.36 | 0.36 | 0.36 | 0.36 |
| Solvent % (w/w) | 0.9 | 0.9 | 0.9 | 0.9 |
| Essential Oil (w/w) | 0 | 0.02 | 0 | 0.02 |
| Fragrance (w/w) | 0 | 0 | 0.03 | 0.03 |
| Sequestring agent (w/w) | 0.09 | 0.09 | 0.09 | 0.09 |
| Water % (w/w) | Q.S. | Q.S. | Q.S. | Q.S. |

As illustrated herein below in Table 7, it is evident that Formulations 8, 23, 24 and 25, embodiments of the present invention, are vastly superior to formulations containing only some of the ingredients described in the present document. Formulations 8, 23, 24 and 25 can still kill all the bacteria when diluted 1/4. The other formulations cannot kill the bacteria even when undiluted (except formulation 17, which cannot once it is diluted 1/2).

From those results, it is evident to those skilled in the art that there is a very significant difference in efficacy between the formulations containing all the ingredients and those that contain only some of them. Likewise, the combination of all the ingredients yields formulations that are much more powerful than what could have been expected when considering the properties of the individual ingredients by themselves.

TABLE 7

| Antimicrobial effect of the formulations | | | | | | | |
|---|---|---|---|---|---|---|---|
| Dilution/Growth | 13 | 14 | 15 | 16 | 17 | 18 | 19 |
| 1 | + | + | + | + | − | + | + |
| ½ | + | + | + | + | + | + | + |
| ¼ | + | + | + | + | + | + | + |
| ⅛ | + | + | + | + | + | + | + |
| Dilution/Growth | 20 | 21 | 22 | 23 | 24 | 8 | 25 |
| 1 | + | + | + | − | − | − | − |
| ½ | + | + | + | − | − | − | − |
| ¼ | + | + | + | − | − | − | − |
| ⅛ | + | + | + | − | + | − | − |

(+) Indicates that the culture tube shows bacterial growth. This indicates that the formulation at that dilution was not able to kill all of the bacteria during the 2 minutes contact time, and thus the bacteria multiplied in the culture tube.
(−) Indicates that the culture tube does not show bacterial growth. This indicates that the formulation at that dilution was not able to kill all of the bacteria during the 2 minutes contact time, and thus the bacteria multiplied in the culture tube.

EXAMPLE 6

Biological Efficacy of Formulation 1 on Selected Microorganisms

The antimicrobial formulations of the present invention exhibit a broad spectrum of activity on a variety of microorganisms. As shown herein below, the efficacy of Formulation 1 against a variety of microorganisms is determined.

TABLE 8

| Microbial activity on various microorganisms | | | | |
|---|---|---|---|---|
| Activity | Standard Method | Group of Microorganisms | Microorganism | 1 |
| Bactericidal | AOAC[1] (Dilution Test) | Bacteria Gram− | Salmonella cholerasuis | Pass |
| | | Bacteria Gram+ | Staphylococcus aureus | Pass |
| Fungicide | AOAC Fungicidal Activity Test | Fungus | Trichophyton mentagrophytes | Pass |
| Virucidal | ASTM[2] Efficacy of Virucidal Agents | Virus | Influenza A | Pass |

[1]Association of Analytical Communities,
[2]American Society for Testing and Materials

EXAMPLE 7

Biological Efficacy of Formulations With Short Contact Time

Various formulations intended to disinfect or sanitize an appendage (ex. skin) do not allow, in real life situation, a long contact time between the formulation and the appendage. For example, the foam, gel, mist, etc. of a hand sanitizer stands on the hands of a subject approximately 30 seconds at best. It is thus crucial that formulations intended to disinfect or sanitize skin have an antimicrobial efficacy in short contact times.

Formulations 9 and 26 to 29 are prepared as illustrated in Table 9 herein below. Formulations 26 to 29 are based on Formulation 9, with decreasing concentrations of thymol. Formulations are then tested for their biological efficacy against *Staphylococcus aureus*. Briefly, 0.1 mL of bacterial culture containing $1\times10^7$, $1\times10^6$, $1\times10^5$, $1\times10^4$ or $1\times10^3$ CFU of *Staphylococcus aureus* is inoculated in a tube containing 10 mL of the given Formulation. The tube's content is then mixed and let stand for 15 seconds (the "contact time"). After 15 seconds, 0.01 mL of tube content is transferred to a tube containing 9 mL of a neutralizing bacterial culture media (Letheen Broth) that stops the antimicrobial action of the formulation and allows microbial growth. Tubes with different concentrations of bacteria (5, 4, 3, 2, 1 logs) are then checked for presence of microbial growth after 72 h. The more potent the antimicrobial effect of the formulation, the more it can kill high logs of the bacteria during the given contact time. The same experiment was done with *Pseudomona aeruginosa*.

TABLE 9

Formulations with decreasing concentration of thymol and antimicrobial efficacy with a 15 seconds contact time

| Formulation | 9 | 26 | 27 | 28 | 29 |
|---|---|---|---|---|---|
| Thymol % (w/w) | 0.24 | 0.17 | 0.1 | 0.05 | 0.01 |
| Surfactant % (w/w) | 0.5 | 0.5 | 0.5 | 0.5 | 0.5 |
| Solvent % (w/w) | 5 | 5 | 5 | 5 | 5 |
| Fragrance (w/w) | 0.09 | 0.09 | 0.09 | 0.09 | 0.09 |
| Water % (w/w) | Q.S. | Q.S. | Q.S. | Q.S. | Q.S. |
| Log reduction against *S. aureus* | 4 | 3 | 1 | 0 | 0 |
| Log reduction against *P. aeruginosa* | 4 | 2 | 1 | 1 | 1 |

As illustrated herein above in Table 9, with a contact time of 15 seconds, Formulations 9, 26 and 27, embodiments of the present invention, are superior to formulations containing lower concentrations of thymol. At thymol concentrations of 0.05 and 0.01, we no longer observe a Log reduction of *S. aureus*, while we still kill 1 Log of *P. aeruginosa*. This can be explained by the structural differences between Gam-positive and Gram-negative bacteria.

From those results, it is evident to those skilled in the art that there is a significant difference in efficacy between the formulations containing decreasing concentration of thymol for a short contact time to achieve antimicrobial efficacy. Likewise, the formulations are more likely to be effective in short contact times when the thymol concentration is above 0.05%.

EXAMPLE 8

Toxicity of the Antimicrobial Formulations

Toxicity tests ($LD_{50}$) are performed on selected ingredients of the antimicrobial formulations of the present invention. Formulation 1 is determined as having a $LD_{50}$ of >15 g/Kg. Based on the Hodge and Sterner toxicity scale, Formulation 1 is considered relatively harmless. As shown in Table 10, the toxicity of isolated ingredients of the formulations from the present invention was tested and they are considered from slightly toxic to relatively harmless. The toxicity of active ingredients present in other disinfectants was also tested and the results are shown in Table 11. These examples are more toxic than each ingredient of the formulations of the present invention.

TABLE 10

Toxicity of various ingredients of Formulation 1 of the present invention

| Ingredients | $LD_{50}$ Oral-rat | Specification |
|---|---|---|
| Thymol | 980 mg/kg | USP, FCC |
| *Origanum* oil | 1850 mg/kg | USP, FCC |
| Citral | 4960 mg/kg | Oxford University |
| Sodium Citrate | >8000 mg/kg | USP, FCC |
| Sodium Lauryl Sulfate | 1288 mg/kg | USP, FCC |
| Sodium Laureth Sulfate | >5000 mg/kg | Hill Top Research |
| Glycol Ether PM | 5 210 mg/kg | WHMIS |

TABLE 10-continued

Toxicity of various ingredients of Formulation 1 of the present invention

| Ingredients | $LD_{50}$ Oral-rat | Specification |
|---|---|---|
| Cetyl Betaine | 1620 mg/kg | Handbook of Green Chemicals |
| 1,3-Propanediol | >15 000 mg/kg | USP |

TABLE 11

Toxicity of various ingredients of known commercial formulations (Prior art)

| Ingredients | $LD_{50}$ Oral-rat | Specification |
|---|---|---|
| Copper sulfate | 352 mg/Kg | ClearTech |
| Formaldehyde | 100 mg/Kg | SicenceLab.com |
| Quaternary ammonium | 366 mg/kg | Lonza Inc |
| Iodine | 14 mg/kg | Fisher Scientific |

EXAMPLE 9

Footbath Product Comparison

Typically, treatment of hoof infection in cattle consists of topical application of antibiotic and footbaths with disinfectant solution to control the transmission of etiological agents in the infected herd. Formulation 5 of the present invention can be used in footbaths for the control of hoof infections in cattle. Copper sulfate pentahydrate and Formaldehyde are two other commonly used solutions in footbaths. Table 12 describes characteristics of Formulation 5 and the two other solutions.

Table 12 lists the following characteristics of Formulation 5, an embodiment of the present invention: i) needs a low dilution; ii) is biodegradable; iii) is not irritant; iv) is not toxic; v) has no carcinogenic effects and vi) the active ingredient is Generally Recognized as Safe (GRAS) by the FDA. These are beneficial features as it renders the formulation efficient to reduce microbial presence while being safe and non-toxic to humans and animals. Copper sulfate and Formaldehyde do not possess these features.

TABLE 12

Characteristics of footbaths solutions

| | Formulation 5 | Copper sulfate pentahydrate[1] | Formaldehyde 37%[2] |
|---|---|---|---|
| Use dilution | 1% | 5-10% | 5% |
| Biodegradability | Readily | N/A | Long term degradation product may arise |
| Irritancy | Non-irritant | Irritant (skin, eye) | Irritant (skin, eye) |
| Toxicity | Non-Toxic Oral, rat: $LD_{50}$ of >15 g/Kg | Toxic Oral, rat: LD50 of 352 mg/Kg | Toxic Oral, rat: LD50 of 100 mg/Kg |
| Carcinogenic effects | Non-Carcinogenic | Classified A2 (Suspected for human) | Non-Carcinogenic |
| Regulatory Status of active ingredients | Generally recognized as safe by FDA | Scrutinized in Europe | Scrutinized in US |

[1]Information: MSDS Copper Sulphate, ClearTech
[2]Information: MSDS Formaldehyde 37%, SicenceLab.com

EXAMPLE 10

In Vitro Efficacy of Formulation 5 and Copper Sulfate Against Treponemes

Digital dermatitis (DD) is one of the major hoof diseases in cattle. Digital dermatitis (DD) also known as foot rot is a highly contagious disease commonly found in sheep, goats, and cattle. Control and treatment of digital dermatitis in cattle is commonly done via footbaths and localized application of antibiotics. A spirochete (*Treponema*) is strongly suspected to be the etiological agent and is found in almost all cases of digital dermatitis. The efficacy of Formulation 5 and Copper Sulfate is evaluated in vitro against a *Treponema*.

The treponemes (*T. phagedaenis*-like bacteria at a concentration of about $10^6$ CFU/ml) were exposed to the solutions in triplicate with a 50% (volume/volume) dilution series. The starting %(w/w) of Formulation 5 is 1% and Copper Sulfate, 5%, i.e. the usual working concentrations for these solutions in footbaths. Exposition to the solutions is 10 minutes and minimal exposure time in presence of 10% and 20% sterilized manure. MICs are determined as the Minimal Inhibitory Concentration of the solutions. MICs for Formulation 5 and Copper Sulfate are presented in Table 13.

TABLE 13

MICs on treponemes of footbath solutions

|  | Formulation 5 | Copper Sulfate |
|---|---|---|
| Working concentration in footbaths | 1% | 5% |
| MIC at Minimal exposure time | 0.00781% | 0.01953% |
| MIC at 10 minutes Exposure time | 0.0026% | 0.03906% |
| MIC at Minimal exposure time with 10% manure | 0.00651% | 0.01302% |
| MIC at Minimal exposure time with 20% manure | 0.00391% | 0.01953% |

As illustrated herein above in Table 13, Formulation 5 and copper sulfate have MICs below the working concentrations in footbaths for these solutions. Also, these formulations can achieve a good efficacy in presence of manure. Formulation 5's MIC is roughly 10 times lower than copper sulfate. From these results, it becomes evident that Formulation 5 can achieve an efficacy against treponemes at lower concentrations than Copper Sulfate in vitro.

EXAMPLE 11

Use of Formulation 5 For Footbaths in Cattle Positive to Digital Dermatitis

Formulation 5, embodiment of the present invention, is evaluated combined to a topical antibiotic treatment to control and treat DD in cattle. Three free-stall herds of dairy cattle positive to DD were selected totalizing 400 animals. Characteristics of the involved herds are presented in Table 14. Formulation 5 is diluted 1:100 in water, and introduced into the baths. During the experiment, cows of each herd go through the footbath 3 times a week. Two hundred cows are allowed to go through the footbaths before the solution is changed to a fresh one. Lesions of posterior hoofs are evaluated throughout the experiment based on the Mortellaro lesion scale: M0, no lesion; M1, small active lesion; M2, large active lesion; M3, healing lesion and M4, chronic lesion. When active lesions (M1 and M2) are observed, tetracycline is applied on the hoofs. The "lesion status" of a cow is determined by the most severe lesion of the two posterior hoofs. Most severe lesion to less severe: M2>M1>M4>M3>M0. At week 0 before the beginning of foot baths and Week 3, lesion score were compiled based on the hoof cage (week 0) and milk parlor (week 3) observations. A statistical McNemar test was done to determine if there was a significant reduction in active lesions M1 and M2 (most severe and painful) in the herds. Results are presented in Table 15.

TABLE 14

Characteristics of herds involved in the study

|  | Herd 1 | Herd 2 | Herd 3 |
|---|---|---|---|
| Total cows | 145 | 275 | 300 |
| Cows observed | 125 | 115 | 165 |
| Prevalence of DD at Day 0 (M1 + M2 lesions) | 53% | 33% | 31% |
| Dimension of foot baths (cm × cm × cm) | 194 × 74 × 16 | 198 × 84 × 15 250 × 100 × 15 | 186 × 76 × 12 |
| Volume of foot baths (L) | 165 | 220 340 | 200 |

TABLE 15

Percentage of cows with absence of lesions (M0), active lesions (M1 + M2), healing lesions (M3) and chronic lesions (M4) at Week 0 and Week 3 after the beginning of footbaths.

|  | Lesion score | Week 0 % of cows | Week 3 % of cows | McNemar test |
|---|---|---|---|---|
| Herd 1 | M0 | 4.9 | 8.7 | — |
|  | M1 + M2 | 53.3 | 8.7 | p < 0.0001 |
|  | M3 | 0.0 | 9.5 | — |
|  | M4 | 41.8 | 73.0 | — |
| Herd 2 | M0 | 2.6 | 10.4 | — |
|  | M1 + M2 | 33.0 | 1.1 | p < 0.0001 |
|  | M3 | 9.6 | 19.8 | — |
|  | M4 | 54.8 | 68.7 | — |
| Herd 3 | M0 | 3.5 | 16.5 | — |
|  | M1 + M2 | 31.2 | 15.2 | p < 0.0001 |
|  | M3 | 20.2 | 15.9 | — |
|  | M4 | 45.1 | 52.4 | — |

As illustrated and described herein above, Formulation 5 diluted 1:100 in water was tested in footbaths for the control of DD in three positive herds. The herds have different starting levels of DD, different foot baths installations, different herd sizes. Nevertheless, in the three herds, after three weeks of footbaths, the percentage of cows with active lesions dropped significantly (p<0.0001). It is evident to those skilled in the art that the level of significance of this finding is very high. It is thus evident that the footbaths of formulation 5, combined to local application of antibiotic, contribute to decrease the most severe lesions in the herds.

Formulation 5 of the present invention has i) beneficial features compared to other foot bath solutions (Table 12), ii) has a higher efficacy in vitro against a DD pathogen (Table 13) and iii) allows a reduction of active DD lesion in cattle. It is evident to those skilled in the art that these findings combined makes formulations of the present invention the preferred solution for foot baths.

EXAMPLE 12 pH Adjusting Agent Containing Compositions

Composition of the present invention containing pH adjusting agents are prepared according to the amounts listed below:

Lactic acid

| | Compositions | | | | |
|---|---|---|---|---|---|
| Ingredient (% w/w) | LA 1 | LA 2 | LA 3 | LA 4 | LA 5 |
| Thymol | 23 | 23 | 23 | 23 | 23 |
| Surfactant | 12 | 11.7 | 11.4 | 11.1 | 10.8 |
| Solvent | 36 | 36 | 36 | 36 | 36 |
| Lactic acid solution ≥85% | 1 | 2 | 3 | 4 | 5 |
| Water | QS | QS | QS | QS | QS |
| pH | 3.92 | 3.6 | 3.41 | 3.24 | 3.18 |
| pH 1:100 dilution in water | 5.93 | 4.2 | 3.7 | 3.39 | 3.34 |

Citric acid

| | Compositions | | | | |
|---|---|---|---|---|---|
| Ingredient (% w/w) | CA1 | CA2 | CA3 | CA4 | CA5 |
| Thymol | 23 | 23 | 23 | 23 | 23 |
| Surfactant | 12 | 11.7 | 11.4 | 11.1 | 10.8 |
| Solvent | 36 | 36 | 36 | 36 | 36 |
| Citric acid solution ≥99.5% | 1 | 2 | 3 | 4 | 5 |
| Water | QS | QS | QS | QS | QS |
| pH | 3.34 | 3.00 | 2.81 | 2.64 | 2.50 |
| pH 1:100 dilution in water | 5.46 | 4.19 | 3.60 | 3.20 | 3.16 |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of preventing or treating a hoof bacterial infection on at least one hoof of a live hoofed animal having a bacterial presence thereon, the method consisting of topically applying to said hoof an antibacterial formulation for a time sufficient to reduce said bacterial presence, said antibacterial formulation consisting of:
   a) one antibacterial isolated or synthetic phenolic compound of natural origin selected from the group consisting of thymol and carvacrol;
   b) at least one surfactant sufficient to form a solution or dispersion of said phenolic compound in water;
   c) a solvent for dissolving said phenolic compound;
   d) a pH adjusting agent; and
   e) a sufficient water quantity to make 100% (w/w);
wherein said pH adjusting agent is selected from the group consisting of hydrochloric acid, boric acid, sulfuric acid, monosodium phosphate, disodium phosphate, trisodium phosphate, monopotassium phosphate, dipotassium phosphate, tripotassium phosphate, Tris(hydroxymethyl) aminomethane (TRIS), paracetic acid, propionic acid, fumaric acid, sorbic acid, benzoic acid, phenylacetic acid, tartaric acid, dehydroacetic acid, glycine, 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid (TES), 2-(N-morpholino)ethanesulfonic acid (MES), N-[Tris(hydroxymethyl)methyl]glycine (Tricine); N-Tris(hydroxymethyl)methyl-3-aminopropanesulfonic acid (TAPS) and 3-N-Morpholino propanesulfonic acid (MOPS), piperazie-N,N'-bis[2-hydroxypropanesulphonic] acid (POPSO), and a combination thereof.

2. The method of claim 1, wherein said formulation comprises from about 0.05% to about 25% (w/w) of said phenolic compound.

3. The method of claim 1, wherein said formulation comprises from about 0.1% to about 15% (w/w) of said surfactant.

4. The method of claim 1, wherein said formulation comprises from about 0.1% to about 40% (w/w) of said solvent.

5. The method of claim 1, wherein said formulation comprises from about 0.01% to about 5% (w/w) of said pH adjusting agent.

6. The method of claim 1, wherein said phenolic compound is thymol.

7. The method of claim 1, wherein said surfactant is selected from the group consisting of sodium lauryl sulfate, sorbitan stearate, sodium laureth sulfate, sarkosyl, cocamidopropyl betaine (CAPB), sodium lauryl ether sulfonate, alkyl benzene sulfonates, nonylphenol ethoxylate, sorbitan esters and ether ethoxylate.

8. The method of claim 1, wherein pH of said antibacterial formulation has a pH from about 1 to about 10.

9. The method of claim 1, wherein said hoof bacterial infection is chosen from a hoof rot, hoof scald, hoof abscesses, and combinations thereof.

10. The method of claim 1, wherein topically applying is with one of a spray, a bath, a footbath, a direct application, a wipe, a cream, an ointment, a gel, or an unguent.

11. The method of claim 1, wherein said hoof bacterial infection is a lesion.

12. The method of claim 11, wherein said lesion is one of an ulcer, a diabetic ulcer, a furuncle, a carbuncle, a fissure, a crack, or a blister.

13. The method of claim 1, wherein said hoof bacterial infection is one of a salmonella infection, an *E. coli* infection, a staphylococcal infection, a spirochete infection, an impetigo, an ecthyma, a carbunculosis, a folliculitis, an erysipelas, an african tick bite fever, an arcanobacterium haemolyticum infection, a botryomycosis, a brucellosis, a canker, a chlamydial infection, a chronic lymphangitis, a chronic recurrent erysipelas, a cutaneous anthrax infection, a cutaneous diphtheria infection, a cutaneous group B streptococcal infection, a cutaneous pasteurella hemolytica infection, a cutaneous streptococcus iniae infection, a dermatitis gangrenosa, a desert sore, a digital dermatitis, a ecthyma gangrenosuma erythrasma, a foot abscess, a furunculosis, a gas gangrene, a glanders, a gram-negative folliculitis, a helicobacter cellulitis, an infected oil gland, an interdigital dermatitis, an interdigital phlegmon, an Italian foot rot a leptospirosis, a Listeria monocytogenes infection, a listeriosis, a melioidosis, a necrotizing fasciitis, a pasteurellosis, a pododermatitis, a primary gonococcal dermatitis, a salmonellosis, a super foot rot, or a toxic shock syndrome.

14. The method of claim 1 wherein said live hoofed animal is livestock.

15. The method of claim 1 wherein said live hoofed animal is cattle.

16. The method of claim 1 wherein said live hoofed animal is a dairy cow.

17. A method of preventing or treating a hoof bacterial infection on at least one hoof of a live hoofed animal having a bacterial presence thereon, the method consisting of topically applying to said hoof an antibacterial formulation for a time sufficient to reduce said bacterial presence, said antibacterial formulation consisting of:
  a) one antibacterial isolated or synthetic phenolic compound of natural origin selected from the group consisting of thymol and carvacrol;
  b) at least one surfactant sufficient to form a solution or dispersion of said phenolic compound in water;
  c) a solvent for dissolving said phenolic compound; and
  d) a sequestering agent;
  e) a pH adjusting agent; and
  f) a sufficient water quantity to make 100% (w/w);
wherein said pH adjusting agent is selected from the group consisting of hydrochloric acid, boric acid, sulfuric acid, monosodium phosphate, disodium phosphate, trisodium phosphate, monopotassium phosphate, dipotassium phosphate, tripotassium phosphate, Tris(hydroxymethyl) aminomethane (TRIS), paracetic acid, propionic acid, fumaric acid, sorbic acid, benzoic acid, phenylacetic acid, tartaric acid, dehydroacetic acid, glycine, 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid (TES), 2-(N-morpholino)ethanesulfonic acid (MES), N-[Tris(hydroxymethyl)methyl]glycine (Tricine); N-Tris(hydroxymethyl)methyl-3-aminopropanesulfonic acid (TAPS) and 3-N-Morpholino propanesulfonic acid (MOPS), piperazie-N,N'-bis[2-hydroxypropanesulphonic] acid (POPSO), and a combination thereof.

18. The method of claim 17, wherein said phenolic compound is from about 0.05% to about 25% (w/w) of said formulation.

19. The method of claim 17, wherein said surfactant is from about 0.1% to about 15% (w/w) of said formulation.

20. The method of claim 17, wherein said solvent is from about 0.1% to about 40% (w/w) of said formulation.

21. The method of claim 17, wherein said formulation comprises from about 0.01% to about 5% (w/w) of said pH adjusting agent.

22. The method of claim 17, wherein said formulation comprises from about 0.01% to about 10% (w/w) of said sequestering agent.

23. The method of claim 17, wherein said phenolic compound is thymol.

24. The method of a claim 17, wherein said surfactant is selected from the group consisting of sodium lauryl sulfate, sorbitan stearate, sodium laureth sulfate, sarkosyl, cocamidopropyl betaine (CAPB), sodium lauryl ether sulfonate, alkyl benzene sulfonates, nonylphenol ethoxylate, sorbitan esters and ether ethoxylate.

25. The method of claim 17, wherein said sequestering agent is selected from the group consisting of ethylene diamine tetraacetic acid (EDTA) sodium salt, sodium gluconate, sodium citrate, citric acid, trisodium NTA, trisodium ethylene disuccinate, sodium phosphate and sodium choleate.

26. The method of claim 17, wherein pH of said antibacterial formulation has a pH from about 1 to about 10.

27. The method of claim 17, wherein said hoof bacterial infection is chosen from a hoof rot, hoof scald, hoof abscesses, and combinations thereof.

28. The method of claim 17, wherein topically applying is with one of a spray, a bath, a footbath, a direct application, a wipe, a cream, an ointment, a gel, or an unguent.

29. The method of claim 17, wherein said hoof bacterial infection is a lesion.

30. The method of claim 17, wherein said lesion is one of an ulcer, a diabetic ulcer, a furuncle, a carbuncle, a fissure, a crack, or a blister.

31. The method of claim 17, wherein said bacterial infection is one of a salmonella infection, an *E. coli* infection, a staphylococcal infection, a spirochete infection, an impetigo, an ecthyma, a carbunculosis, a folliculitis, an erysipelas, an african tick bite fever, an arcanobacterium haemolyticum infection, a botryomycosis, a brucellosis, a canker, a chlamydial infection, a chronic lymphangitis, a chronic recurrent erysipelas, a cutaneous anthrax infection, a cutaneous diphtheria infection, a cutaneous group B streptococcal infection, a cutaneous pasteurella hemolytica infection, a cutaneous streptococcus iniae infection, a dermatitis gangrenosa, a desert sore, a digital dermatitis, a ecthyma gangrenosuma erythrasma, a foot abscess, a furunculosis, a gas gangrene, a glanders, a gram-negative folliculitis, a helicobacter cellulitis, an infected oil gland, an interdigital dermatitis, an interdigital phlegmon, an Italian foot rot a leptospirosis, a Listeria monocytogenes infection, a listeriosis, a melioidosis, a necrotizing fasciitis, a pasteurellosis, a pododermatitis, a primary gonococcal dermatitis, a salmonellosis, a super foot rot, or a toxic shock syndrome.

32. The method of claim 17 wherein said live hoofed animal is livestock.

33. The method of claim 17 wherein said live hoofed animal is cattle.

34. The method of claim 17 wherein said live hoofed animal is a dairy cow.

* * * * *